United States Patent [19]
Colacino et al.

[11] Patent Number: 6,037,348
[45] Date of Patent: Mar. 14, 2000

[54] INHIBITION OF VIRAL REPLICATION

[75] Inventors: Joseph Matthew Colacino, Indianapolis; Steven Duane Hatch, New Palestine; William Joseph Hornback, Fishers; Mark Ayer Muesing, Greenwood; John Edwin Munroe; Kirk Alan Staschke, both of Indianapolis; Joseph Chiou-Chung Tang, Carmel, all of Ind.

[73] Assignee: Eli Lilly and Company, Indianapolis, Ind.

[21] Appl. No.: 08/795,731

[22] Filed: Feb. 5, 1997

Related U.S. Application Data

[60] Provisional application No. 60/011,442, Feb. 9, 1996, and provisional application No. 60/017,119, May 6, 1996.

[51] Int. Cl.[7] .......................... A01N 43/42; A01N 37/00; A61K 31/44; A61K 31/21
[52] U.S. Cl. .......................... 514/301; 514/277; 514/284; 514/290; 514/301; 514/510; 514/557
[58] Field of Search ..................................... 514/301, 277, 514/284, 290, 510, 557

[56] References Cited

PUBLICATIONS

Bodian, et al., *Biochemistry,* vol. 32, 2967–2978 (1993).
Bullough, et al., *Nature,* vol. 371, 37–42 (1994).
Prosch, et al., *Febs Letters,* vol. 267, No. 1, 19–21 (1990).
Ott, et al., *Antiviral Research,* vol. 24, 37–42 (1994).
Carr, et al., *Cell,* vol. 73, 823–832 (1993).
Cohen, et al., *Science,* vol. 263, 488–489 (1994).
Bethell, et al., *Biochem. & Biophys. Res. Comm.,* vol. 206, No. 1, 355–361 (1995).
Daniels, et al., *Cell,* vol. 40, 431–439 (1985).
Schoch, et al., *J. of Biol. Chem.,* vol. 268, No. 13, 9267–9274 (1993).
Ramalho–Santos, et al., *Biochemistry,* 32, 2771–2779 (1993).
Bodian et al., "inhibition of the fusion–inducing conformational changes of influenza hemagglutinin by benzoquinones and hydroquinones", Biochemistry, 32, 2967–2978, 1993.
White et al., "Fusion mechanism of the influenza hemagglutinin: Inhibitor design" (Abstract), J. Cell Biochem., Suppl 16C, 111, 1992.

*Primary Examiner*—Jose' G. Dees
*Assistant Examiner*—Marina Lamm
*Attorney, Agent, or Firm*—Janet T. McClain

[57] ABSTRACT

The present invention provides a method of inhibiting influenza and flaviviral replication based on a mechanism of action in which HA-mediated fusion or E protein mediated fusion is inhibited by a fusion inhibiting agent which binds, complexes or otherwise becomes associated with HA or E protein during the translation of the target protein and/or its vesicular transport.

5 Claims, 9 Drawing Sheets

FIGURE 1

Per Cent Inhibition vs. CONCENTRATION COMPOUND F RESISTANT

CONCENTRATION (µg/ml)

FIGURE 2

Per Cent Inhibition vs. CONCENTRATION
Wild Type Virus

FIGURE 3A

Per Cent Inhibition vs. CONCENTRATION
COMPOUND C RESISTANT

FIGURE 3B

Per Cent Inhibition vs. CONCENTRATION
COMPOUND D RESISTANT

FIGURE 4

|     | 2 of 6 | 3 of 6 | 1 of 6 |
|-----|--------|--------|--------|
| PB2 | Kaw    | Kaw    | Kaw    |
| PB1 | Kaw    | Kaw    | Kaw    |
| PA  | Kaw    | Kaw    | Kaw    |
| HA  | WSN    | WSN    | WSN    |
| NP  | Kaw    | Kaw    | Kaw    |
| NA  | Kaw    | WSN    | WSN    |
| M   | Kaw    | Kaw    | Kaw    |
| NS  | Kaw    | Kaw    | WSN    |

Figure 1:
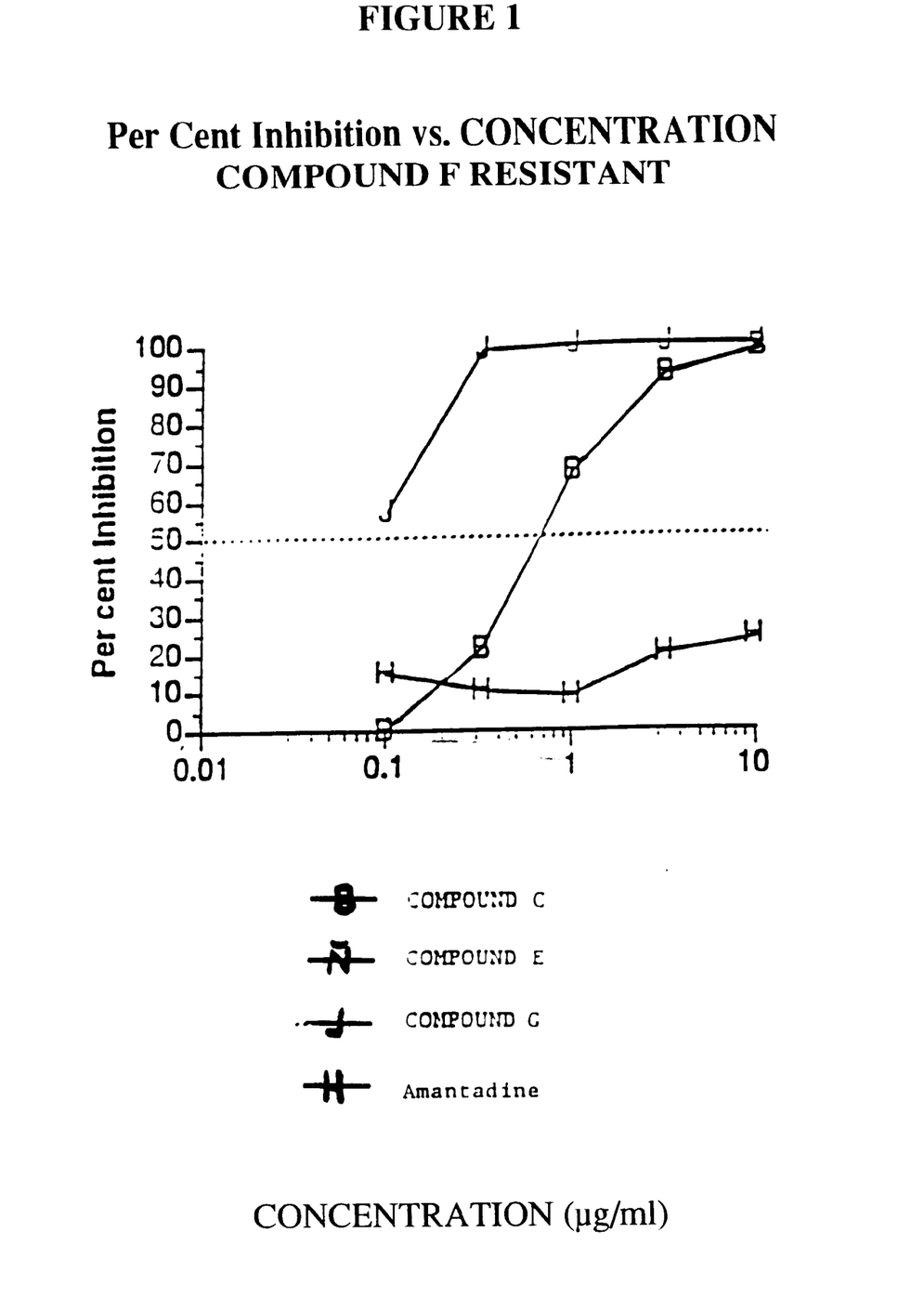
FIG. 1—depicts a graph of percent inhibition vs concentration ($\mu$/ml) for COMPOUNDS C, E, G and Amantadine against Amantadine-resistant influenza virus.
Figure 2:
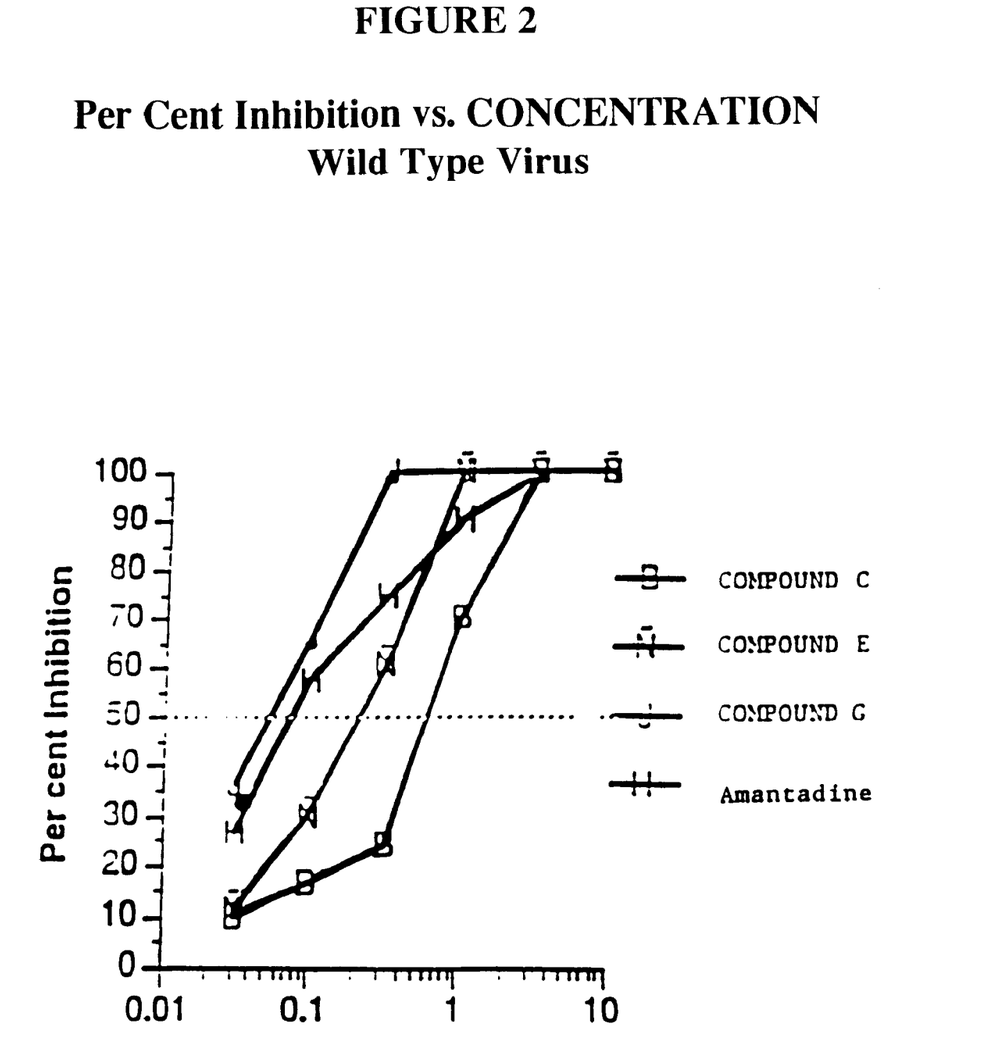
FIG. 2—depicts a graph of percent inhibition vs concentration ($\mu$g/ml) for COMPOUNDS C, E, G and Amantadine against wild type influenza virus.
Figure 3A:
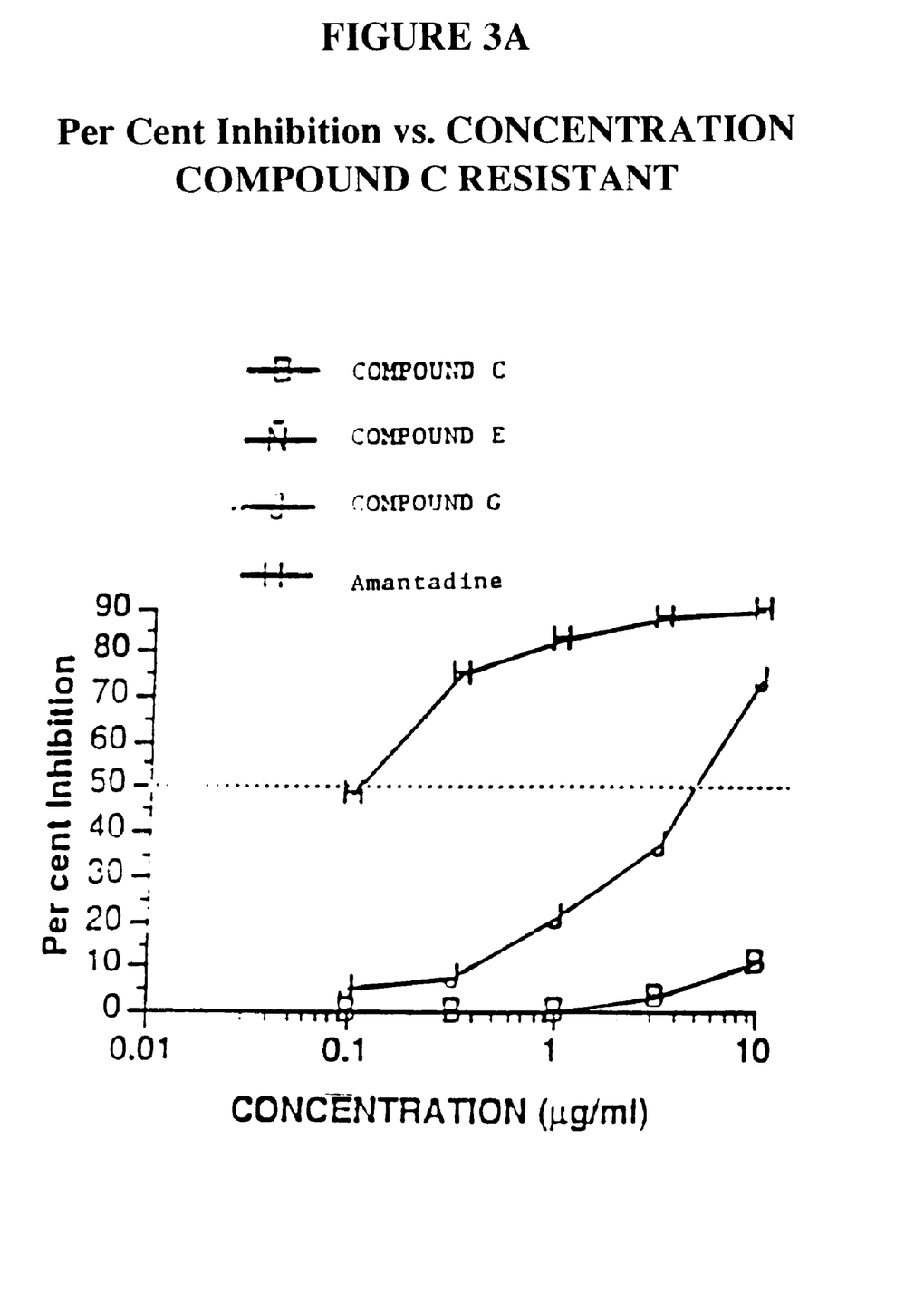
FIG. 3A—depicts a graph of percent inhibition vs concentration (μg/ml) for COMPOUNDS C, E, G and Amantadine against COMPOUND C-resistant influenza virus.
Figure 3B:
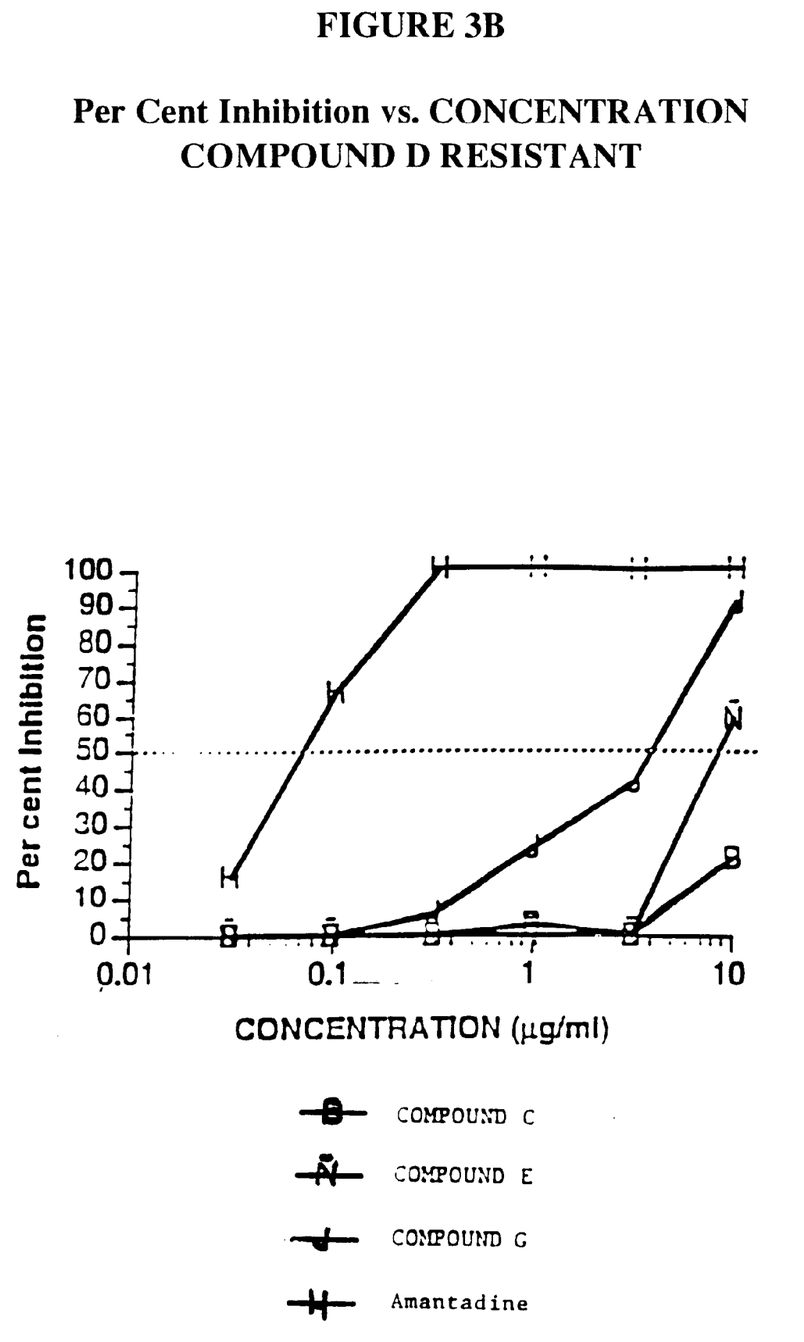
FIG. 3B—depicts a graph of percent inhibition vs concentration (μg/ml) for COMPOUNDS C, E, G and Amantadine against COMPOUND D-resistant influenza virus.
Figure 4:
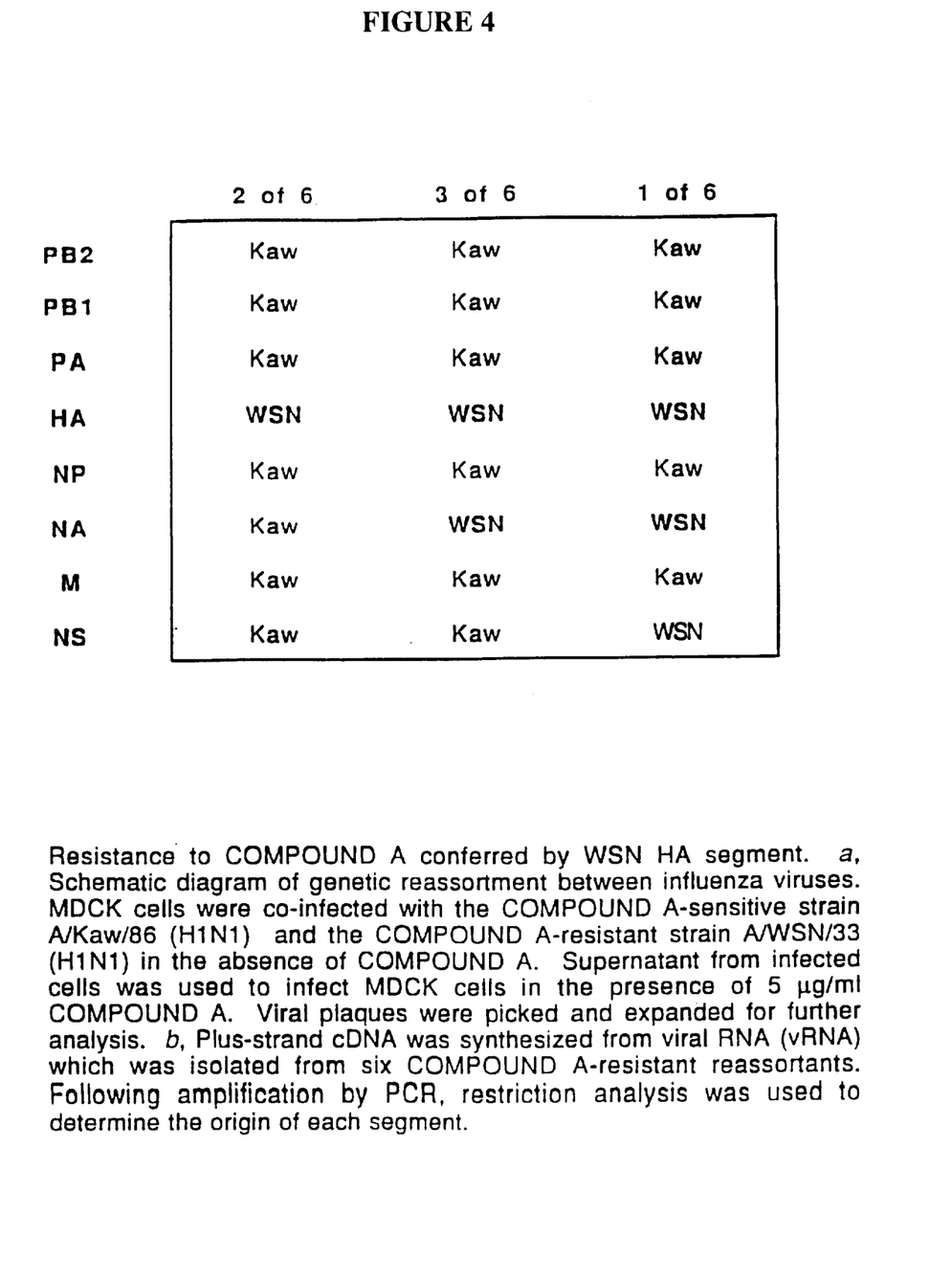
FIG. 4—depicts the results from the Reassortant Experiment.

Resistance to COMPOUND A conferred by WSN HA segment. a, Schematic diagram of genetic reassortment between influenza viruses. MDCK cells were co-infected with the COMPOUND A-sensitive strain A/Kaw/86 (H1N1) and the COMPOUND A-resistant strain A/WSN/33 (H1N1) in the absence of COMPOUND A. Supernatant from infected cells was used to infect MDCK cells in the presence of 5 μg/ml COMPOUND A. Viral plaques were picked and expanded for further analysis. b, Plus-strand cDNA was synthesized from viral RNA (vRNA) which was isolated from six COMPOUND A-resistant reassortants. Following amplification by PCR, restriction analysis was used to determine the origin of each segment.

FIGURE 5

Figure 5:
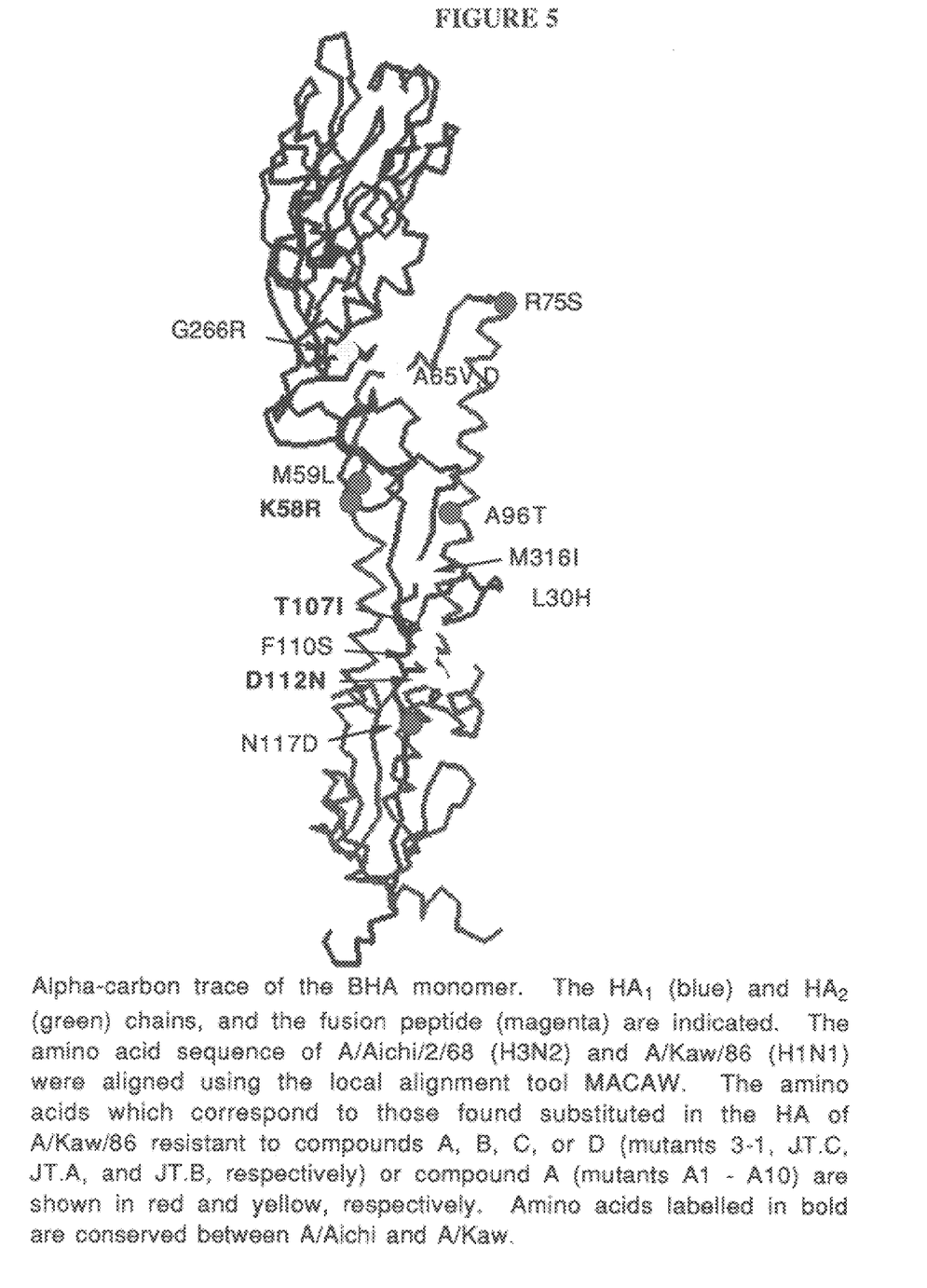
FIG. 5—depicts the location of the amino acid substitutions on HA of drug resistant viruses.

Alpha-carbon trace of the BHA monomer. The HA₁ (blue) and HA₂ (green) chains, and the fusion peptide (magenta) are indicated. The amino acid sequence of A/Aichi/2/68 (H3N2) and A/Kaw/86 (H1N1) were aligned using the local alignment tool MACAW. The amino acids which correspond to those found substituted in the HA of A/Kaw/86 resistant to compounds A, B, C, or D (mutants 3-1, JT.C, JT.A, and JT.B, respectively) or compound A (mutants A1 - A10) are shown in red and yellow, respectively. Amino acids labelled in bold are conserved between A/Aichi and A/Kaw.

FIGURE 6

Figure 6:
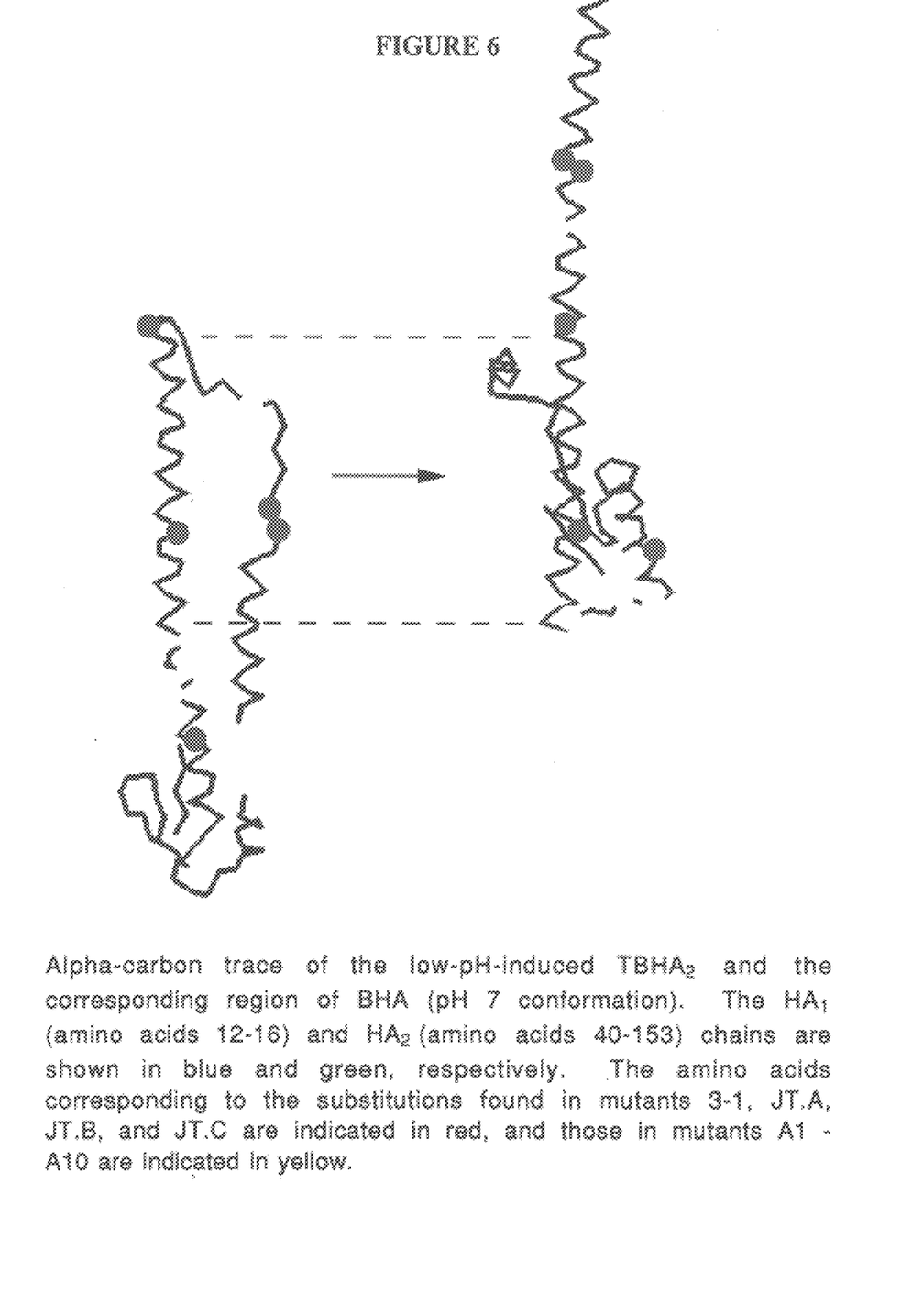
FIG. 6—depicts the locations of the amino acid substitutions on HA of drug resistant viruses in Form A and Form B.

Alpha-carbon trace of the low-pH-induced $TBHA_2$ and the corresponding region of BHA (pH 7 conformation). The $HA_1$ (amino acids 12-16) and $HA_2$ (amino acids 40-153) chains are shown in blue and green, respectively. The amino acids corresponding to the substitutions found in mutants 3-1, JT.A, JT.B, and JT.C are indicated in red, and those in mutants A1 - A10 are indicated in yellow.

FIGURE 7

Figure 7:
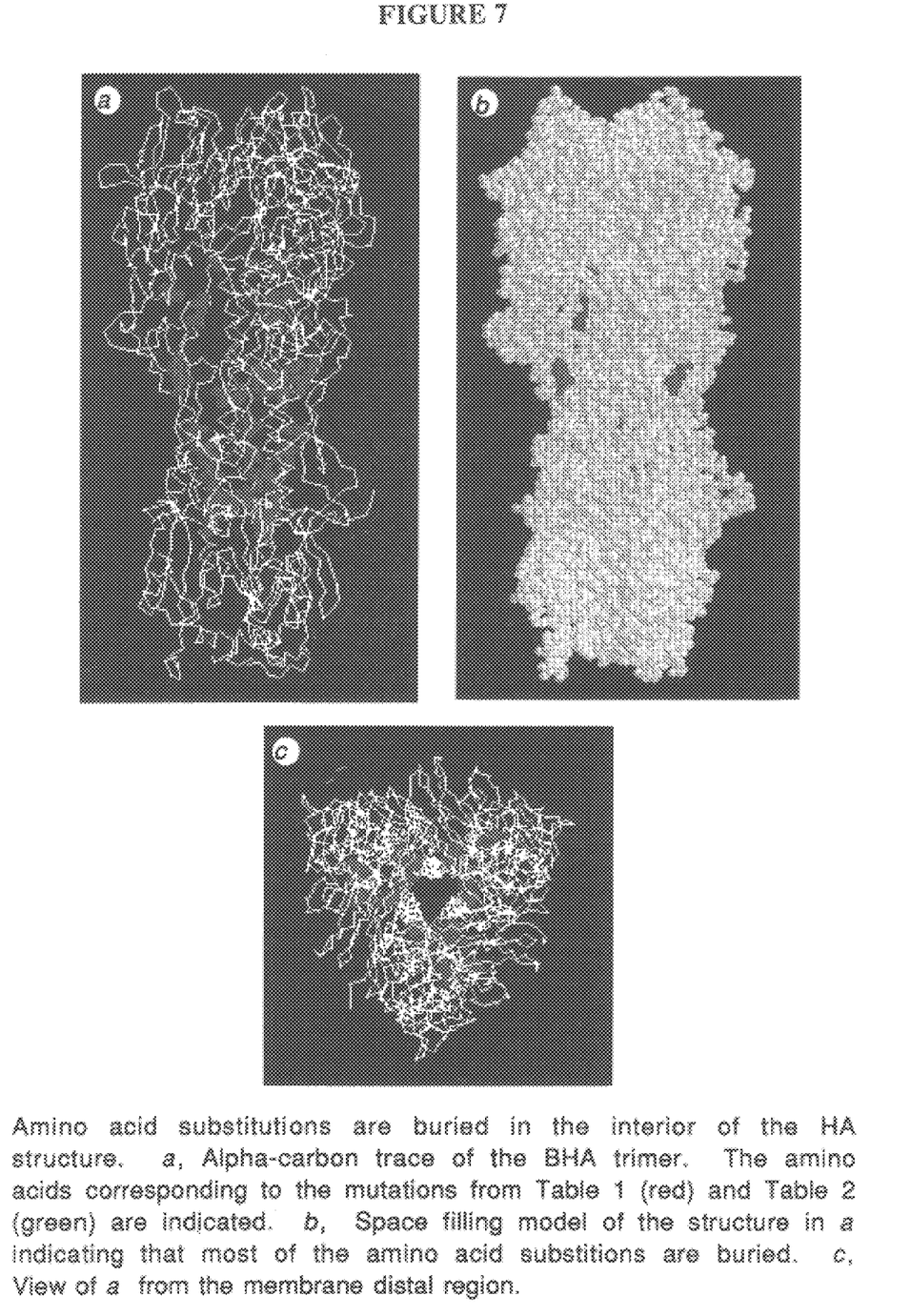
FIG. 7—depicts the amino acid substitutions that are buried in the interior of the trimeric HA structure.

Amino acid substitutions are buried in the interior of the HA structure. a, Alpha-carbon trace of the BHA trimer. The amino acids corresponding to the mutations from Table 1 (red) and Table 2 (green) are indicated. b, Space filling model of the structure in a indicating that most of the amino acid substitions are buried. c, View of a from the membrane distal region.

FIGURE 8

Figure 8:
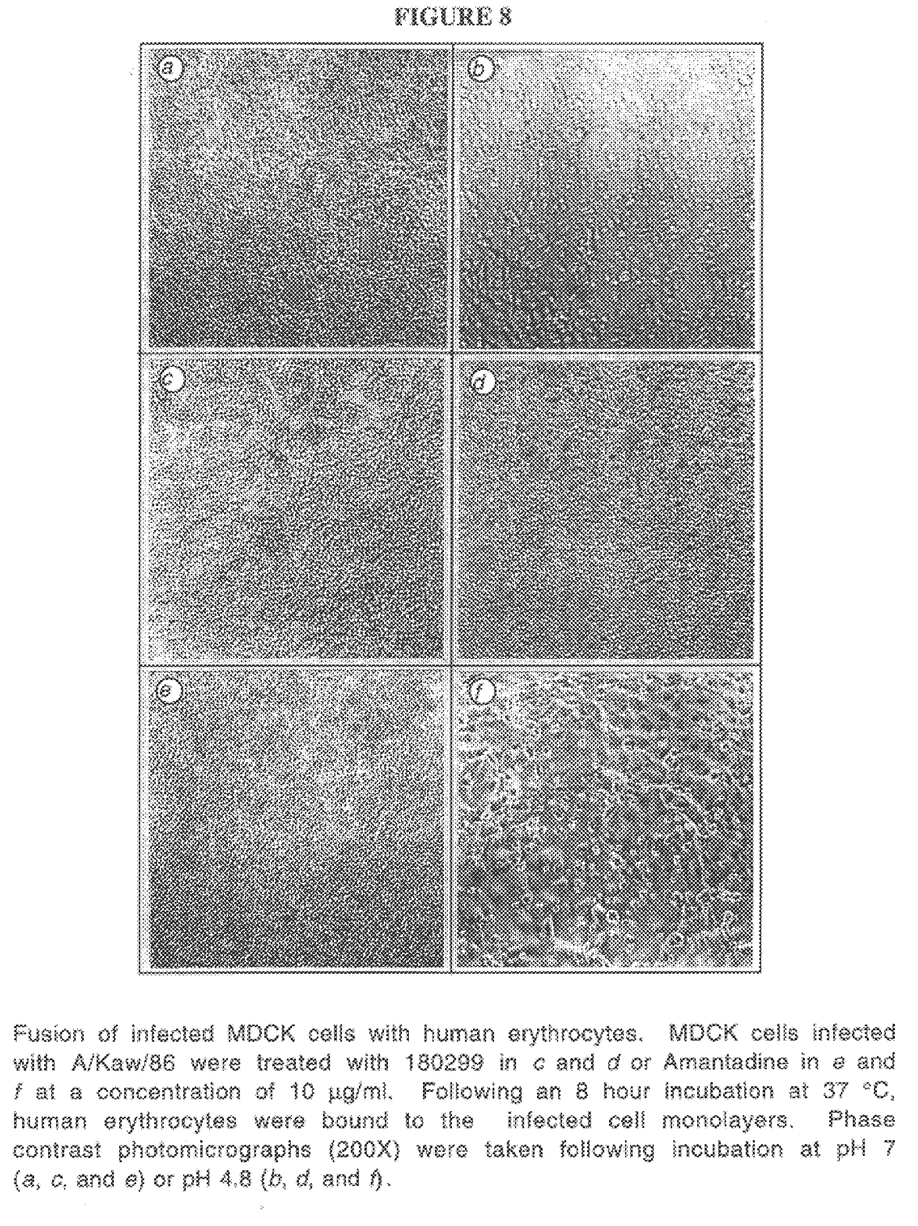
FIG. 8—depicts the results from a Red Cell Fusion Assay.

Fusion of infected MDCK cells with human erythrocytes. MDCK cells infected with A/Kaw/86 were treated with 180299 in c and d or Amantadine in e and f at a concentration of 10 μg/ml. Following an 8 hour incubation at 37 °C, human erythrocytes were bound to the infected cell monolayers. Phase contrast photomicrographs (200X) were taken following incubation at pH 7 (a, c, and e) or pH 4.8 (b, d, and f).

INHIBITION OF VIRAL REPLICATION

This application claims benefit of Provisional application Ser. No. 60/011,442 Feb. 9, 1996. This application claims benefit of Provisional application. Ser. No. 60/017,119 May 6, 1996

BACKGROUND OF THE INVENTION

Influenza and flaviviruses cause a variety of infectious diseases for which there is no adequate therapeutic agent. The disadvantages of existing treatments include the onset of clinical resistance within thirty six hours and the ineffectiveness of the agents against influenza B. Killed influenza virus vaccines have been available for over sixty years. However, these vaccines have not lessened the morbidity, mortality or severe financial loss caused by this disease. It follows that an agent which treats or prevents an influenza or flavivirus infection or is effective at preventing the clinical symptoms associated therewith will result in a significant benefit to society.

Currently, the only compounds approved for the therapeutic and prophylactic treatment of influenza infections are the adamantanes: amantadine and rimantadine. These compounds inhibit influenza A by inhibiting the function of the M2 ion channel activity of the virus. Amantadine is a potent in vitro inhibitor of influenza A virus as demonstrated by standard antiviral assays such as the plaque reduction assay. Amantadine is effective in reducing the duration of fever and other systemic complaints including but not limited to myalgia (muscular ache) and fatigue when administered to individuals infected with influenza A within forty-eight hours of the onset of clinical symptoms. It has also been observed that amantadine results in a one hundred-fold decrease of virus titer in the nasal washes of human volunteers infected with wild-type influenza virus which correlates with a dramatic decrease in fever score. Thus, in vitro influenza inhibition is predictive of useful in vivo effects, i.e. a reduction of the clinical symptoms associated with the influenza infection.

The present invention derives from the fact that orthomyxoviruses such as influenza and flavivirues such as bovine diarrheal virus and hepatitis C virus are enveloped viruses in which the virus envelope must be fused with the endosomal membrane of the host cell in order to initiate the process of introducing the virus' genetic information into the cell. Because this process is common to all enveloped viruses, it is an attractive target for antiviral chemotherapy. The fusion domain of the envelope glycoprotein of influenza, hemagglutinin (HA) and the envelope protein (E protein) of flaviviruses have been well characterized. See e.g., White J. M, Annu. Rev. Physiol. vol. 52, pages 675–697 (1990); Rev, F. A. et al. Nature, 375, 291–298 (1995), which is herein incorporated by reference.

Influenza virus HA and flavivirus E proteins provide at least two distinct functions: 1) recognition of the host cell receptor, i.e., sialic acid residues on glycoconjugates, and 2) fusion of the viral envelope with the endosomal membrane. Both functions are essential, for example, in the propagation of influenza virus in vitro and in vivo. During influenza viral maturation, monomeric HA is inserted into a lipid bilayer, post-translationally modified and oligomerized into a trimer of identical subunits (trimeric HA). The infectivity of the progeny influenza virus is contingent upon a site-specific cleavage of HA by host cell protease(s). This cleavage results in the formation of two polypeptide chains, HA1 and HA2, which remain associated by non-covalent interactions as well as by an intermolecular and intramolecular disulfide bonds.

It has been established that influenza HA and E protein have two functionally relevant conformations. One conformation exists as a metastable structure at neutral pH and mediates receptor recognition. Following receptor mediated binding to the host cell, the virus is transported to the endosomal compartment where it encounters an acidic environment. The low pH triggers a dramatic structural rearrangement that results in the formation of the other, more stable conformation. It is this structural rearrangement, for example from Form A to Form B of HA in the case of influenza, that allows the fusion domain of HA to directly interact with the endosomal membrane enabling the release of viral genetic information into the host cell cytoplasm. These considerations lend themselves to the development of a strategy for antiviral intervention based on the abrogation of HA-mediated or E protein-mediated fusion of virus-host membranes.

SUMMARY OF THE INVENTION

A method of inhibiting flavivirus replication which comprises administering to a producer host cell an effective amount of a fusion inhibiting agent such that the progeny virus is unable to replicate whereas the parent virus is able to replicate.

A method of inhibiting influenza replication which comprises administering to a producer host cell an effective amount of a fusion inhibiting agent such that the progeny virus is unable to replicate whereas the parent virus is able to replicate.

A method of inactivating the fusion domain of hemagglutinin or E protein to a fusion inhibiting agent in a producer host cell such that an inactive conformer of said proteins in the progeny virus is stable at endosomal pH.

A method of inhibiting influenza replication which comprises stabilizing Form A trimer of hemagglutinin of a progeny virus in a producer host cell such that the hemagglutinin in the progeny virus upon maturation is non-fusogenic whereas the hemagluttinin in the parent virus is fusogenic.

A method of inhibiting flavivirus replication which comprises stabilizing a non-fusogneic form of an E protein in a progeny virus.

A method of inhibiting fusion of a progeny influenza or flavivirus with a host cell which comprises administering to a producer host cell an effective amount of a fusion inhibiting agent.

A method of inhibiting fusion of a progeny influenza or flavivirus with a host cell which comprises stabilizing the fusion domain of a hemagglutinin or Protein E of the progeny virus such that the hemagglutinin or Protein E in the progeny virus upon maturation is non-fusogenic whereas the hemagluttinin or Protein E in the parent virus is fusogenic.

DETAILED DESCRIPTION OF THE INVENTION

The file of this patent contains at least one drawing executed in color. Copies of this patent with color drawings will be provided by the Patent and Trademark Office upon request and payment of the necessary fee.

The term "replication" means the action or process of reproducing or duplicating the viral RNA and the associated viral proteins by the host cell and includes within its definition the assembly of infective progeny virus particles.

The term "stabilizing" means preventing or retarding the structural rearrangement of HA or E protein, for example from HA Form A to Form B, thus preventing the fusion domain of HA from becoming fusogenic.

The term "administering" means exposing a producer host cell to a fusion inhibiting agent. The term exposing includes bringing the cell and agent in proximity to each other.

The term "fusogenic" means a structural form of HA or E protein which contains a fusion domain which is able to interact with the endosomal membrane of the host cell and cause the release of viral genetic information into the host cell cytoplasm.

The term "non-fusogenic" means a structural form of HA or E protein that contains a fusion domain that is not able to interact with the endosomal membrane and cause the release of viral genetic information into the host cell cytoplasm.

The term "progeny virus" means the virus that is made by the producer host cell after fusion of the parent virus with the host cell.

The term "E protein" or "envelope protein" refers to a major surface protein on flavivirues that mediates target cell receptor binding and viral membrane fusion. E proteins form dimers on the surface of mature viruses at physiological pH. However, exposure to a pH environment less than about 6.5 induces a conformational change in E protein that is believed to be critical in the fusion of flaviviral and endosomal membranes.

The term "fusion inhibiting agent" means an agent such as a chemical molecule which binds, complexes or otherwise becomes associated with HA or E protein during the translation of the target protein and/or its vesicular transport during which oligomerization of the protein takes place ultimately leading to inhibition of the conformational switch of E protein or of HA Form A to Form B.

The term "flavivirus" means a genus of animal viruses that includes, but is not limited to, west nile virus (WNV), tick-borne encephalitis virus, hepatitis C virus (HCV), yellow fever virus, and bovine diarrheal virus (BVDV). Flaviviruses are enveloped, comprise RNA genomes, and fuse with target host cells by a mechanism involving E proteins, such as E1 and E2. Fusion of viral and endosomal membranes is optimal at low pH.

The term "effective amount" as used herein, means an amount of a fusion inhibiting agent which inhibits the fusion of the virus to the host cell. The influenza and flavivirus inhibition contemplated by the present method includes both therapeutic and prophylactic treatment, as appropriate. The specific dose of compound administered according to this invention to obtain therapeutic and/or prophylactic effects will, of course, be determined by the particular circumstances surrounding the case, including, for example, the compound administered, the route of administration, the condition being treated and the individual being treated. A typical daily dose (administered in single or divided doses) will contain a dosage level of from about 0.01 mg/kg to about 50 mg/kg of body weight of an active compound of this invention. Preferred daily doses generally will be from about 0.05 mg/kg to about 20 mg/kg and ideally from about 0.1 mg/kg to about 10 mg/kg.

The compounds can be administered by a variety of routes including oral, rectal, transdermal, subcutaneous, intravenous, intramuscular and intranasal. The compounds of the present invention are preferably formulated prior to administration. Therefore, another embodiment of the present invention is a pharmaceutical formulation comprising an effective amount of a compound of formula I or a pharmaceutically acceptable salt thereof and a pharmaceutically acceptable carrier, diluent or excipient therefor.

The active ingredient in such formulations comprises from 0.1% to 99.9% by weight of the formulation. By "pharmaceutically acceptable" it is meant that the carrier, diluent or excipient is compatible with the other ingredients of the formulation and not deleterious to the recipient thereof.

The following compounds were identified as inhibiting virus replication by stabilizing the fusion domain of hemagglutinin (HA) or E protein of an immature progeny virus such that the immature progeny virus upon maturation contains non-fusogenic hemagglutinin or E protein and is unable to replicate.

COMPOUND A

COMPOUND B

-continued

COMPOUND C

COMPOUND D

COMPOUND E

COMPOUND G

COMPOUND H

COMPOUND I

-continued

COMPOUND J

COMPOUND K

Compound C has been described in French Patent FR 7031 (690721); Compound H is described in Can. J. Chem. 65(1) 124–30 (1987).

Preparation 1

Compound E can be prepared from compound C by methods known in the art and by methods disclosed herein. For example, compound C, 775 mg, was dissolved in approximately 15 ml of glacial acetic acid, charged to a pressure resistant glass bottle, and 100 mg of 5% rhodium on carbon added. The bottle was flushed with hydrogen gas, sealed, and pressurized to approximately 60 psi. The reaction was heated to 60 degrees centigrade and agitated overnight. The reaction was cooled, vented, filtered, and the solvent removed by rotary evaporation. The crude product was purified by dissolving it in 10 ml of 1N sodium hydroxide, washing with diethyl ether, and acidifying the aqueous layer with 5N hydrochloric acid. The aqueous layer was extracted with 3 portions of methylene chloride and the combined extracts washed with brine. The solvent was removed by rotary evaporation to yield a brown oily product. NMR, mass spec., and elemental analysis confirmed the product.

Antiviral Plaque Assay

The in vitro anti-influenza activities of COMPOUND A, COMPOUND B, COMPOUND C and amantadine were evaluated using a standard plaque assay such as described in Hayden et al., Antimicrob. Agents Chemother., vol. 17, pages 865–870, (1980), herein incorporated by reference. In this assay, influenza virus-infected Madin Darby canine kidney (MDCK) cells were untreated or treated with serial dilutions of each compound. The concentration of compound required to inhibit viral plaque formation by 50% ($IC_{50}$) was determined from the linear regression line of the plot of compound concentration versus percent inhibition of plaque formation. In addition, the $IC_{50}$ can be determined by the method of Reed and Muench, Am. J. Hyg, vol. 27, 493–497 (1938) which is herein incorporated by reference. These compounds displayed potent activity against influenza A/Kawasaki. These viruses also displayed antiviral activity against other influenza A and B viruses. Table 1, below provides a summary of these data.

TABLE 1

Antiviral Activity of COMPOUND A, COMPOUND C, and COMPOUND B

| Virus | type | COMPOUND C IC50 (μg/ml) | COMPOUND A IC50 (μg/ml) | COMPOUND B IC50 (μg/ml) | Amantadine IC50 (μg/ml) |
|---|---|---|---|---|---|
| A/KAW | H1N1 | 0.07 | <0.032 | 0.024 | 0.036 |
| A/WSN | H1N1 | >10 | >10 | >10 | >10 |
| A/NWS | H1N1 | >10 | >10 | ~9.59 | >10 |
| A/FM/1/47 | H1N1 | 0.15 | <0.032 | 0.18 | 0.13 |
| A/AA | H2N2 | 0.069 | <0.032 | 0.15 | 0.037 |
| A/AICHI | H3N2 | ~10 | ~10 | ~7.26 | 0.076 |
| B/Lee | | >10 | ~1.23 | ~1.08 | >10 |
| B/Maryland | | 6.34 | ~2.70 | ~2.23 | >10 |
| B/GL | | >10 | 5.65 | 2.83 | >10 |

Resistance Studies

In order to establish whether the biological activity of these compounds was directed against a viral target or the host cell, influenza A/Kawasaki viruses were selected for resistance to a member of each class of these compounds. The resistance studies led to two conclusions. First, the antiviral activity of the tested compounds was mediated through a viral function as opposed to a cellular function. Second, the tested compounds exerted antiviral activity through a common mechanism of action.

The antiviral activity stems from the inhibition of a viral function because sequential passage of the wild-type virus in stepwise increases of compound concentration followed by plaque purification resulted in the selection of highly drug-resistant viruses. Furthermore, the resistant viruses were found to be cross-resistant, suggesting that the antiviral activity of the compounds stems from a common mechanism of action. FIGS. 1, 2, 3A and 3B are graphs of percent inhibition vs concentration (μg/ml) of the tested compound.

Further studies demonstrated that these compounds retained full antiviral activity even when added up to 8 hours post-infection, indicating that the mechanism of action for antiviral activity is mediated late in the viral replication cycle.

Molecular Characterization of Drug-Resistant Virus Mutants

1. Drug Resistance Maps to the HA Gene Segment of Influenza A Virus

Sequence studies were performed in order to map the viral genome mutations relevant for the drug-resistant phenotype. Viral RNA from wild-type, COMPOUND C-resistant influenza, COMPOUND D- resistant, COMPOUND B-resistant or COMPOUND A-resistant A/Kawasaki virus was used as a template for the synthesis of cDNA by reverse transcriptase. The cDNA representing individual viral gene segments was amplified using segment specific PCR primers and the PCR products were sequenced using a cycle sequencing protocol.

Nucleotide changes were found in the HA2 segment of HA in each of the drug-resistant viruses as indicated in Table 2, below. The correlation of HA sequence alterations with high level drug resistance and viral cross-resistance was substantiated further by sequence analysis of the HA segment from COMPOUND A-resistant mutants. Independent isolates of A/Kawasaki (n=10) were selected for growth in a high concentration of COMPOUND A (5 μg/ml) using a single passage protocol. The HA gene segment of each of these viruses was sequenced and again, in each case the mutant RNA segment contained at least one sequence alter-ation. Table 3 provides the amino acid substitutions in COMPOUND A-resistant mutants. This establishes a direct correlation between HA sequence alteration(s) and high level drug resistance.

TABLE 2

Amino Acid substitutions in the HA of Drug Resistant Mutants

| Compound | Mutant[a] | HA$_1$ | HA$_2$ |
|---|---|---|---|
| C | JT.A[b] | — | K58R/M59L (K, T)[c] |
| D | JT.B | — | A65V (Q) |
| B | JT.C | — | M59I/N117D (T, K) |
| A | 3-1 | — | R75S/A96T/N117D (G, A, K) |

[a]Influenza virus strain A/Kawasaki/86 was selected for resistance to COMPOUND C, COMPOUND D, COMPOUND B, or COMPOUND A by passage in Madin-Darby canine kidney (MDCK) cells in step-wise increases of compound and plaque purified three times. Virion RNA (vRNA) was purified from mutant or parent A/Kawasaki/86 viruses and used as template for the synthesis of plus-strand DNA. The plus-strand DNA was then amplified by PCR and sequenced by double-stranded cycle sequencing. Sequence analysis of vRNA segments NS, M, NP, NA, and HA of JT.A virus revealed mutations leading to amino acid substitutions in the HA.
[b]Virus JT.A which is resistant to COMPOUND C is also cross-resistant to COMPOUND D.
[c]The amino acid sequences of HA from A/Kaw/86 (H1N1) and A/Aichi/2/68 (H3N2) were aligned using the local alignment tool MACAW. The amino acids in parentheses indicate the corresponding amino acids in the HA of A/Aichi/2/68.

TABLE 3

Amino Acid Substitutions in Mutants Resistant to COMPOUND A

| Mutant[a] | HA$_1$ | HA$_2$ | Drug Dependent[c] |
|---|---|---|---|
| A1 | G266R (S)[b] | — | - |
| A2 | — | F110S (L) | +[d] |
| A3 | L30H/M3161 (T, L) | — | + |
| A4 | — | T1071 (T) | - |
| A5 | — | F110S (L) | - |
| A6 | — | A65D (Q) | - |
| A7 | L30F (T) | — | - |
| A8 | — | D112N (D) | + |
| A9 | G266R/M3161 (S, L) | — | - |
| A10 | — | T1071 (T) | - |

[a]MDCK cells were infected with a single plaque forming unit (pfu) of influenza virus strain A/Kaw/86 in the presence of 5 μg/ml COMPQUND A and plaque purified once. Virion RNA (vRNA) was purified from the drug resistant or parent viruses as described in Table 1.
[b]The amino acids in parentheses indicate the corresponding amino acids in the HA of A/Aichi/2/68.
[c]Titration of mutant viral stocks was performed in MDCK cells ± COMPOUND A.
[d]Mutant A2 showed a similar number of plaques ± COMPOUND A but showed an altered plaque morphology in absence of COMPOUND

| | |
|---|---|
| G = Gly | D = Asp |
| L = Leu | A = Ala |
| H = His | N = Asn |
| M = Met | S = Ser |
| F = Phe | T = Thr |
| R = Arg | Q = Gln |

Reassortment Experiments

The role of HA in the resistance of influenza A virus to the antiviral activity of COMPOUND A was further substantiated by reassortant experiments. In these studies, influenza A/WSN/33 which is naturally resistant to COMPOUND A, was inactivated with ultraviolet radiation and inoculated onto MDCK cells along with influenza A/Kawasaki/86 which is sensitive to COMPOUND A.

The doubly-infected cells were incubated in the absence of COMPOUND A until a virus induced cytopathic effect was observed. Virus in the cell culture fluid was serially diluted and used to infect MDCK cells in the presence of COMPOUND A (5 μg/ml). The resultant viral plaques were picked and expanded. Viral RNA was obtained from the expanded plaques and copied into cDNA using reverse transcriptase. The resulting cDNA was amplified using segment specific PCR primers and each of the amplified gene segments was subjected to restriction enzyme analysis and characterized by comparison with gene segments from each of the initial viruses.

These studies established that all reassortant viruses which were resistant to COMPOUND A contained the HA segment from influenza A/WSN/33 and some resistant isolates contained only the HA segment. These results are summarized in FIG. 4. It follows that the HA gene from the resistant virus A/WSN/33 was necessary and sufficient to confer the drug resistant phenotype.

2. Location of Mutations in Drug Resistant Viruses: Implications for Mechanism of Action It is evident that the inhibition of HA is essential to the antiviral activity since all of the mutations in drug resistant viruses mapped to the HA gene segment. None of the mutations mapped to the sialic acid receptor binding domain of HA indicating that these compounds do not interfere with receptor recognition. Moreover, experiments have shown that hemagglutination of chicken red blood cells by influenza virus is not affected by the fusion inhibiting agents.

The mutations found in the HA segment of both COMPOUND C-resistant and COMPOUND A-resistant viruses are dispersed throughout the HA primary amino acid sequence, clustering in one of two regions of the tertiary structure of HA-Form A. These two regions are: 1) the interface between HA1 and HA2 which is critical for maintaining the integrity of Form A at neutral pH, and 2) near the fusion domain of HA2. These mutations are displayed in FIG. 5. FIG. 6 shows the locations of these mutations in Form A and Form B. FIG. 7 shows that these mutations are buried in the interior of the trimeric HA structure.

Inhibition of HA mediated fusion, resulting in the inability of the virus to introduce its genetic material into the host cell cytoplasm, can be accomplished by at least five mechanisms of action. These mechanisms of action are as follows:

-continued

4. Invention agent (a) → monomer → trimer Form A → ~~endosomal pH~~ → [trimer Form B]*

5. Alternative Hypothesis agent (a) → monomer → ✗ trimer Form A → endosomal pH → [trimer Form B]*

The Form B mechanism of action involves inhibiting the fusion process by inactivating HA Form B. This mechanism involves a direct interaction of Form B with an inhibitor such as a small molecule. Such an inhibitor would be expected to be operative immediately following the conformational switch.

The triperiden (Norikan®) and Bodian et al. mechanisms of action involve inhibiting the conformational change from Form A to Form B with a drug by stabilizing the conformation structure of Form A over that of Form B within the endosome. There are at least two ways that Form A may be stabilized. For example, the triperiden mechanism involves elevating the endosomal pH thus preventing the conformational change to Form B. The Bodian mechanism involves a drug interacting with the Form A trimer resulting in the stabilization of Form A and thereby preventing the conformational change to Form B. This hypothesis is described in Bodian et al., Biochemistry, vol. 32, pages 2967–2978 (1993).

In the present invention, the monomeric HA is exposed to a fusion inhibiting agent during translation resulting in the formation of a Form A trimer that is bonded, complexed or otherwise associated with one or more fusion inhibiting agents. The locations of the mutations in COMPOUND A- and COMPOUND C-resistant viruses are consistent with the inhibiton of the conformational switch from Form A to Form B in the endosomal compartment. Time-of-drug-addition studies indicated that the target of these compounds is within the infected producer cell but that the antiviral activity becomes manifest only during the next round of infection in newly infected cells. It follows that the present invention does not involve a direct interaction with the HA Form A trimer of the producer host cell. Rather, the compounds which exemplify the present invention affect the Form A trimer that is produced by the producer host cell and used by the progeny virus.

In support of the above mechanism by which these fusion inhibiting agents directly interact with HA, a subset of drug-resistant viruses exhibit a drug-dependent phenotype i.e. in the presence of drug, they replicated to titers which were greater than 100-fold higher than without drug.

In addition, the following Assay was carried out to verify the above mechanism.

Red Cell Fusion Assay

Fusion of infected MDCK cells with human erythrocytes was monitored as follows: confluent monolayers of MDCK cells was infected at 37° C. for 1 hour with A/Kawasaki/86 at a multiplicity of infection of approximately 25. The monolayer was then rinsed twice with minimal essential medium (MEM) containing 0.2% bovine albumin (BA) and replaced with MEM containing 0.2% BA, 2 µg/ml trypsin, and COMPOUND A at a concentration of 10 µg/ml. Following an 8 hour incubation at 37° C., the monolayer was rinsed once as above and a solution of 1% human erythrocytes in phosphate buffered saline (PBS) was added. Following a 15 minute incubation at room temperature, the monolayers were washed extensively with PBS (3–5 times) until all unbound erythrocytes were washed from the uninfected control monolayer. The infected cells were then inspected for the presence of bound erythrocytes. The cell monolayer was incubated with pre-warmed MEM at pH 7 or 4.8 at 37° C. Following a 5 minute incubation, the medium was replaced with MEM at neutral pH and the monolayers were incubated at 37° C. Cell monolayers were monitored for fusion of infected MDCK cells with bound human erythrocytes and phase-contrast photomicrographs (200×) were taken two hours later.

Results

COMPOUND A had no effect on the expression of HA on the infected cell surface as evidenced by erythrocyte binding on cells treated with COMPOUND A (see panel c vs. a in FIG. 11). However, treatment of infected MDCK cells with COMPOUND A resulted in the inhibition of the low pH-induced fusion of MDCK cells with human erythrocytes, a process which is mediated by HA (see panel b vs. d). These results are consistent with the hypothesis that COMPOUND A binds to HA during the folding and/or the oligomerization of HA and thus prevents membrane fusion.

In addition, the Red Cell Fusion Assay was conducted with A/WSN/33, a virus that was established to be resistant to the antiviral activity of COMPOUND A (see Table 1). It was observed that COMPOUND A showed no effect on the fusion of human erythrocytes with A/WSN/33-infected MDCK cells. These results further support the hypothesis that the antiviral activity of COMPOUND A is mediated through inhibition of the fusogenic function of influenza virus HA.

An alternate mechanism involves inhibiting the monomeric HA from forming the Form A trimer. Inhibiting the formation of the Form A HA would necessarily inhibit the fusion of the virus with the host producer cell since trimeric HA is essential to the fusion process.

The experiments detailed above establish that the present invention involves a novel mechanism of action by which HA-mediated fusion is inhibited by a fusion inhibiting agent which binds, complexes or otherwise becomes associated with HA during the translation of the target protein and/or its vesicular transport during which oligomerization of the protein ultimately leading to the inhibition of the conformational switch of Form A trimer to the Form B trimer. It is believed that the fusion inhibiting agent binds, complexes or otherwise becomes associated to a domain of the protein which is inaccessible in the fully formed oligomeric state. Consequently, these compounds will not be active after the fully assembled HA trimer is inserted into the envelope of the mature virion. Consistent with the described mechanism of action, COMPOUND A tested inactive when pre-incubated with infectious virions in a cell-free medium.

Inhibition of Flaviviruses

BVDV belongs to the flavivirus group of viruses which are similar in overall genomic organization and gene expression to hepatitis C virus. BVDV has been used in tissue culture virus replication assays as a surrogate virus for HCV. Like influenza, infection of a host cell by a flavivirus requires that a particular viral membrane glycoprotein (i.e. E protein) mediate fusion of the flaviviral and endosomal membranes. Flavivirus fusion is reminiscent of influenza infections in that flavivurus infections are stimulated by low pH and are associated with conformational changes in E protein.

Compound A and related compounds were tested for their ability to inhibit replication of BVDV in tissue culture. Compound A inhibited replication in MDBK cells by 50% at a concentration of 3.5 µg/ml and by 90% at a concentration of 13.4 µg/ml (See Table 4). All compounds were dissolved in DMSO to yield stock solutions of 20 µg/ml. Drug dilutions were carried out in DMSO; "no drug" controls consisted of DMSO alone. In all cases the final concentration of DMSO was 0.1%.

TABLE 4

Anti-BVDV Activity of COMPOUND A and Related Compounds

| Compound | IC50 (µg/ml)[a] | IC50 (µg/ml)[b] | TC50 (µg/ml)[c] |
|---|---|---|---|
| A | 3.56 | 13.47 | 51.84 |
| I | 4.94 | 16.03 | 32.02 |
| J | 5.25 | 8.9 | 30.75 |
| K | 14.99 | 50.99 | >100 |

[a]Concentration of compound required to inhibit virus replication by 50% as determined by the CPE/XTT assay.
[b]Concentration of compound required to inhibit virus replication by 90% as determined by the CPE/XTT assay.
[c]Concentration ot compound which is 50% toxic to the MDBK host cell as determined by the XTT assay.

Antiviral activity was evaluated using either the CPE/XTT protection assay or the plaque reduction assay. For the CPE/XTT protection assay the ability of the test compound to protect the cells from virus-induced cytopathic effect was evaluated. MDBK cells were plated in Minimal Essential Medium (MEM) containing penicillin/streptomycin, sodium bicarbonate and 10% horse serum in 96-well flat-bottomed microtiter tissue culture plates, at a density of approximately 10,000 cells per well. The cells were infected with BVDV (ATCC VR-534) at a multiplicity of infection of 0.1 plaque forming units per cell. Medium containing serial dilutions of the compound was added, and the cultures were incubated for 3 to 4 days at 37° C. until extensive virus-induced cytopathic effects were evident in the no-drug controls. Antiviral activity was quantified by the XTT assay in which 50 ul of freshly prepared XTT-PMS medium [(1 mg of 2,3-bis(methoxy-4-nitro-5-sulfophenyl)-2H-tetrazolium-5 (XTT) per ml and 25 nM phenazine methosulfate (PMS) in serum free MEM)] was added to each well. The plates were incubated for 2 to 3 hours at 37° C. Color development, correlated to metabolically active cells, was evaluated spectrophotometrically by recording optical density at 450 nm. The concentration of drug required to prevent 50% of the cytopathic effect ($IC_{50}$) or 90% of the cytopathic effect ($IC_{90}$) was calculated from the linear portion of each dose response curve.

For the antiviral plaque reduction assay, MDBK cells were seeded into 6 well tissue culture plates and incubated in MEM growth medium. When the cells were confluent, the medium was removed and an inoculum containing approximately 100 plaque forming units of BVDV was added to each well. After allowing the virus to adsorb for 1–2 hours at room temperature, an overlay containing DMSO carrier alone or the indicated concentration of drug in equal parts of 1.5% melted agarose and 2X MEM containing 5% horse serum (v/v) was added to the cells. When the overlay solidified, the plates were incubated at 37° C. for 2 to 4 days until plaque formation was evident in the no-drug control.

We claim:
1. A method of inhibiting flavivirus replication which comprises administering an effective amount of a fusion inhibiting agent to a producer host cell which produces a non-fusogenic form of an E protein such that an immature progeny virus produced by the host cell is unable to replicate upon maturation whereas a parent virus is able to replicate, wherein the fusion inhibiting agent is selected from the group consisting of -continued -continued and 2. The method according to claim 1 wherein the effective amount is a dosage level from about 0.01 mg/kg to about 50 mg/kg of body weight.

3. The method according to claim 1 wherein the effective amount is a dosage level from about 0.05 mg/kg to about 20 mg/kg of body weight.

4. The method according to claim 1 wherein the effective amount is a dosage level from about 0.1 mg/kg to about 10 mg/kg of body weight.

5. The method according to claim 1 wherein a means for administering the fusion inhibiting agent is selected from the group consisting of oral, rectal, transdermal, subcutaneous, intravenous, intramuscular and intranasal.

* * * * *